United States Patent [19]

Okii et al.

[11] 4,231,789
[45] Nov. 4, 1980

[54] METHOD FOR PROTECTING CROPS FROM SUFFERING DAMAGES

[76] Inventors: Mitsuyoshi Okii, 2611-6, Oyama-machi, Machida-shi, Tokyo; Tatsuya Onitake, 1-3, Kiso-machi, Machida-shi, Tokyo; Masanobu Kawai, 1-12-2, Asahi-machi, Machida-shi, Tokyo; Tetsuo Takematsu, 612, Mine-machi, Utsunomiya-shi, Tochigi-ken Tokyo; Makato Konnai, 3645, Tsuruta-machi, Utsunomiya-shi, Tochigi-ken, all of Japan

[21] Appl. No.: 948,781

[22] Filed: Oct. 5, 1978

Related U.S. Application Data

[62] Division of Ser. No. 807,743, Jun. 17, 1977, abandoned.

[30] Foreign Application Priority Data

Jun. 17, 1976 [JP] Japan .................................. 51/70405
Jun. 17, 1976 [JP] Japan .................................. 51/70406
Aug. 5, 1976 [JP] Japan .................................. 51/92752
Jan. 24, 1977 [JP] Japan .................................. 52/5785

[51] Int. Cl.$^2$ ............................................. A01N 33/04

[52] U.S. Cl. ...................................... 71/121; 71/88; 71/92; 71/94; 71/113

[58] Field of Search ......................................... 71/121

[56] References Cited

U.S. PATENT DOCUMENTS

3,178,855  4/1965  Siegel .................................... 71/121

FOREIGN PATENT DOCUMENTS

2705034  8/1977  Fed. Rep. of Germany .............. 71/121

OTHER PUBLICATIONS

Akii et al., "Prevention of Crop Plant Damage, etc.", (1977), CA 88, No. 165488v, (1978).

*Primary Examiner*—Glennon H. Hollrah
*Attorney, Agent, or Firm*—Craig and Antonelli

[57] ABSTRACT

Crops are protected from suffering various damages by applying polyamine compounds such as long-chain alkylenediamines. By the use of said polyamine compounds, various effects can be obtained, for example, reduction of cold-weather damage or frost damage to crops, retardation of fading of green color of green crops, reduction of damage from photochemical oxidants to crops, retardation of wilting of leaves of crop plants, etc.

7 Claims, No Drawings

METHOD FOR PROTECTING CROPS FROM SUFFERING DAMAGES

This is a division of application Ser. No. 807,743, filed June 17, 1977, now abandoned.

BACKGROUND OF THE INVENTION

1. Field of the Invention

The present invention relates to a method for protecting crops from suffering various damages. More particularly, it relates to a method for protecting crops from suffering various damages such as, cold-weather damage or frost damage, fading of green color, damage from photochemical oxidants, wilting of leaves, and the like, which comprises applying polyamine compounds represented by the following general formula (I):

$$H_2N-R_1-NH_2 \qquad (I)$$

[wherein $R_1$ represents a group of —$(CH_2)_n$— (wherein n represents an integer of 4–18), —$(CH_2)_3NH(CH_2(4-,-(CH_2)_4-NH(CH_2)_4-,-(CH_2)_3NH(CH_2)_3NH(CH_2)_3-,-(CH_2(_3NH(CH_2)_4NH(CH_2)_3-,$

a fluorenylene group, a naphthylene group, or a group of

or an acid addition salt thereof.

2. Description of the Prior Art

Further investigations have led to the discovery that the application of the compounds of the general formula (I) and the acid addition salts thereof to the crops provides various effects such as reduction of cold-weather damage or frost damage to crops, retardation of fading of green color of green crops, reduction of injury to crops from photochemical oxidants, retardation of wilting of leaves of crop plants, etc.

Several methods or chemicals for protecting crops from suffering various damages other than injury from herbicides are known. For example, as the chemicals for reducing cold-weather damage to crops, there are known CCC [(2-chloroethyl)trimethylammonium chloride], B-995 (N-dimethylaminosuccinamic acid), Amo-1618 [(4-hydroxy-5-isopropyl-2-methylphenyl)trimethylammonium chloride, 1-piperidine carboxylate)], etc. [Nobutaka Takahashi et al.; *Shokubutsu Choseibusshitsu no Engei-teki Riyo* (Horticultural Use of Plant Growth Regulator), p. 225 issued by Seibundo Shinko Sha (Oct. 30, 1973)]. As the method for reducing frost damage, there are known the method of using smoke (Japanese Laid-Open patent application No. 39,245/76), etc. As the chemicals for retarding fading of green crops, there are known kinetin ($N^6$-furfurylaminopurine) [Yoshio Masuda, et al.; *Shokubutsu Horumon* (Plant Hormone), p. 219, issued by Asakura Shoten (Dec. 20, 1971)]etc. As the chemicals for reducing injury to crops from photochemical oxidants, there are known xanthone (Japanese Laid-Open patent application No. 31,030/75), etc. As the chemicals for retarding wilting of leaves of crop plants, there are known kinetin [Yoshio Masuda et al.; *Shokubutsu Horumon* (Plant Hormone), p. 230, issued by Asakura Shoten (Dec. 20, 1971)], and the like.

However, the compounds of the general formula (I) and the acid addition salts thereof of the present invention are different in structure from any of these compounds.

SUMMARY OF THE INVENTION

The present invention relates to a method for protecting crops from suffering various damages which comprises applying polyamine compounds represented by the general formula (I) or the acid addition salts thereof (hereinafter the compound(s) represented by the general formula (I) or the acid addition salt(s) thereof are merely referred to as polyamine compound(s)).

Effects which can be obtained by the present invention are, for example, reduction of cold-weather damage or frost damage to crops, retardation of fading of green crops, reduction of damage from photochemical oxidants to crops, retardation of wilting of leaves of crop plant, and the like.

DESCRIPTION OF THE INVENTION

In the definition of the polyamine compound, the group of —$(CH_2)_n$— includes a tetramethylene group, a hexamethylene group, an octamethylene group, a nonamethylene group, a decamethylene group, a dodecamethylene group, a tetradecamethylene group, a hexadecamethylene group, an octadecamethylene group, etc. As the fluorenylene group, a 2,7-fluorenylene group, etc. and, as the naphthylene group, a 1,8-naphthylene group, etc. may be mentioned.

Typical examples of the compounds represented by the general formula (I) are as follows: tetramethylenediamine, pentamethylenediamine, hexamethylenediamine, octamethylenediamine, nonamethylenediamine, decamethylenediamine, dodecamethylenediamine, tetradecamethylenediamine, hexadecamethylenediamine, octadecamethylenediamine, 1,8-diaminonaphthalene, 1,2-diaminonaphthalene, 2,7-diaminofluorene, spermidine, homospermidine, spermine, N,N'-diguanyl-1,8-diaminooctane, p,p'-diaminomethylbiphenyl, etc.

As the acid addition salts of the compounds of the general formula (I), inorganic or organic acid addition salts such as hydrochlorides, sulfates, carbonates, phosphates, formates, acetates, propionates, etc. may be mentioned.

According to the present invention, the polyamine compounds may be used as it is, but is usually used as a composition with adjuvants for agricultural chemicals and if necessary, fertilizers, insecticides, fungicides, miticides, nematocides, herbicides, antiviral agents, plant growth regulators, attractants, etc.

Adjuvants include a solvent, a carrier, a surface active agent, an adhesive agent, etc.

The compositions for protecting crops (hereinafter referred to as crop-protecting compositions(s)) are prepared by admixing one or more of the polyamine compounds, in effective amounts, with adjuvants to provide formulations suitable for ready and efficient application to protect crops using conventional applicator equipment. Such formulations include an aqueous formulation, a wettable powder, an embrocation, an emulsifiable concentrate, granules, etc. The formulations are actually used as a liquid (a solution, a suspension, an emulsion, etc.) or a solid (a powder, etc.).

Solid compositions such as wettable powders are prepared by admixing the polyamine compound mainly with carriers such as bentonite, talc, diatomaceous earth, synthetic alumina, phenol resin, white carbon, etc. to give homogeneous mixture.

Liquid compositions such as aqueous formulations are prepared by admixing the polyamine compound mainly with a suitable solvent.

Any solvent may be used so long as it is inert to the polyamine compounds, herbicides, etc. and it does not give injury to crops.

Examples of the solvent are water, n-hexane, cyclohexane, benzene, xylene, chlorobenzene, ethylene glycol, ethyl ether, acetone, ethyl acetate, dimethylformamide, isophorone, etc.

The crop-protecting composition in any formulation may preferably also include a surface active agent as a wetting, dispersing or emulsifying agent.

The surface active agents employed can be cationic surface active agents such as stearyltrimethylammonium chloride, alkylpicolinium chloride, etc., nonionic surface active agents such as alkylaryl polyether alcohol, polyoxyethylene alkylphenyl ether, alkylphenol polyethylene glycol ether, polyoxyethylene sorbitan fatty acid ester, sorbitan fatty acid ester (sorbitan monolaurate, sorbitan monopalmitate, etc.), amphoteric surface active agents such as alkylbetaine, etc., and anionic surface active agents such as sodium lauryl sulfate, sodium alkylbenzenesulfonate (e.g., sodium dodecylbenzenesulfonate, etc.), sodium lignin sulfonate, etc. In particular, cationic surface active agents and nonionic surface active agents are preferable.

As the adhesive agents, casein, carboxymethylcellulose, glue, etc. may be used.

The crop-protecting composition is usually applied as a spray to the locus to be protected. The crop-protecting composition may be also used by impregnating crops, by mixing with soil or by embrocating crop seeds.

The polyamine compound is, of course, applied in an amount sufficient to exert the desired protective action. The amount of the polyamine compound contained in the crop-protecting composition should be varied depending upon the crops to which the crop-protecting composition is applied, application place, season, weather, growth state of crops and weeds, etc.

The polyamine compound is to be contained in aforesaid various formulations such as an aqueous formulation, a wettable powder, etc. in a concentration of at least 0.01%, preferably 0.1–80% by weight. Such a formulation may be, if necessary, diluted with aforesaid solvent such as water up to a concentration of 10 ppm based on the effective ingredient without losing the activity.

In case of using the crop-protecting composition liquid for spraying, the polyamine compound may be contained in the liquid with a concentration of $10^{-4}$–1.5 mol/l.

In case of impregnation, a concentration of $10^{-4}$–$10^{-2}$ mol/l as polyamine compound is suitable.

The polyamine compound may be generally applied to the locus to be protected in an amount of 0.1–1500 mol/hectare as the polyamine compound.

The polyamine compound gives the effects on various kinds of crops. Examples of crops to which the polyamine compound is applicable include gramineous crops such as wheat, rice, barley, oat, two-rowed barley, rye, corn, pasture, japanese millet, etc., beans such as soybean, dry bean, Lima bean, Pole bean, Snap bean, pea, peanut, navy bean, etc., leafy vegetables such as spinach, trefoil, lettuce, Brasica Rapa L. var. Komatsuna Hara, *Chrysanthemum coronarium* L. var. spatiosum Baley, etc., tomato, radish, asparagus, onion, cucumber, pumpkin, alfalfa, flax, buckwheat, rapeseed, cotton, mulberry, tobacco, taro, sweet potato, fruit trees such as apple, oranges (grape-fruit, etc.), cherry, grape, apricot, peach, pear, etc., and flowering plants such as zeranium, poinsettia, carnation, saintpaulia, marguerite, etc.

The present invention will be described in more detail in reference to the case of using the polyamine compound as an agent for protecting crops from suffering damages other than injury from herbicides.

The method for applying the polyamine compound and crops to which the polyamine compound is applicable are described before. As for application time, it may be used according to the necessity of each case.

For example, in case that the polyamine compound is used in order to reduce cold-weather damage or frost damage, it should be applied when such a situation is actually forecast.

Details are described on each effect.

(1) Reduction of cold-weather damage and frost damage (Test Example 10):

Growth delay due to low temperature of frost can be mitigated.

Of the polyamine compounds, polymethylenediamines having 7 to 12 carbon atoms show the strongest action of reducing cold-weather damage and frost damage.

As the particularly suitable crops for this purpose, rice, wheat, barley, two-rowed barley, rye, radish, buckwheat, rapeseed, cotton, etc. can be mentioned.

(2) Retardation of fading of green crops (Test Examples 11, 12):

Fading of green color of cut leaves of crop plant is regarded.

Further, when applied to crops under cultivation, the physiological activity protector increases in some cases the green density of the leaves.

Particularly suitable crops are leafy vegetables such as spinach, trefoil, lettuce, Chrysanthemum coronarium L. var. spatiosum Baley, etc., radish, and the like.

(3) Reduction of injury from photochemical oxidants (Test Example 13):

Photochemical oxidants like ozone cause in some cases minute spots, bleaching spots or necrotic spots on the leaves of crop plant. The polyamine compound effectively reduces such injury.

Particularly suitable crops are broad leaf crops such as leafy vegetables (e.g. spinach, trefoil, lettuce, Brasica. Rapa L. var. Komatsuna Hara), tobacco, taro, etc.

(4) Retardation of wilting of leaves (Test Example 14):

The polyamine compound may be applied to crops when a long period of high temperature and fine weather is expected, or to crops which are on the way of transplantation in a state separated from soil.

Particularly suitable crops are broad leaf crops such as mulberry, tobacco, leafy vegetables, etc., flower plants, etc.

The present invention will be further illustrated by the following examples.

EXAMPLE 1 (AQUEOUS FORMULATION TYPE)

An aqueous formulation type crop-protecting composition prepared by uniformly mixing 5 parts by weight of octamethylenediamine with 95 parts by weight of water.

EXAMPLE 2 (AQUEOUS FORMULATION TYPE)

An aqueous formulation type crop-protecting composition prepared by uniformly mixing 0.5 g of octamethylenediamine, 0.03 ml of a spreader (Rino; made by Nihon Noyaku Co., Ltd., consisting of 20% by weight of alkylphenol polyethylene glycol ether, 12% by weight of lignin sulfonate and 68% by weight of water, etc.), and 100 ml of water.

EXAMPLE 3 (AQUEOUS FORMULATION TYPE)

An aqueous formulation type crop-protecting composition prepared by uniformly mixing 1 g of octamethylenediamine and 100 ml of a hydroponic solution (Hoagland solution).

EXAMPLE 4 (WETTABLE POWDER TYPE)

A wettable powder type crop-protecting composition prepared by uniformly mixing and finely pulverizing 30 parts by weight of octamethylenediamine, 5 parts by weight of Runox-p-65-L (trade name of sodium alkylbenzenesulfonate; made by Toho Chemical Industry Co., Ltd.), 30 parts by weight of talc and 35 parts by weight of bentonite.

EXAMPLE 5 (WETTABLE POWDER TYPE)

A wettable powder type crop-protecting composition prepared by uniformly mixing 30 parts by weight of octamethylenediamine, 5 parts by weight of sodium dodecylbenzenesulfonate and 65 parts by weight of bentonite.

EXAMPLE 6 (SEED EMBROCATION TYPE)

A seed embrocation type crop-protecting composition prepared by uniformly mixing 50 parts by weight of octamethylenediamine, 25 parts by weight of Triton X 120 (trade name of alkylaryl polyether alcohol; made by Rohm & Haas Co.) and 25 parts by weight of white carbon. 2 Parts by weight of this crop-protecting composition is added to 98 parts by weight of wheat seeds to embrocate the seed surface. Thus embrocated seeds containing 1% of the effective ingredient are obtained.

EXAMPLE 7 (EMULSIFIABLE CONCENTRATE TYPE)

An emulsifiable concentrate type crop-protecting composition prepared by mixing 50 parts by weight of octamethylenediamine, 30parts by weight of dimethylformamide, 15 parts by weight of xylene and 5 parts by weight of Nissan Nonion NS 206 (trade name of polyoxyethylene alkylphenyl ether; made by Nippon Oil & Fats Co., Ltd).

EXAMPLE 8 (GRANULE TYPE)

A granule type crop-protecting composition prepared by uniformly mixing and pulverizing 3 parts by weight of octamethylenediamine, 3 parts by weight of white carbon, 2 parts by weight of sodium ligninsulfonate and 92parts by weight of bentonite, adding thereto a small amount of water, kneading the mixture, granulating by a push type granulator, and drying.

EXAMPLE 9 (GRANULE TYPE)

A granule type crop-protecting composition prepared by uniformly mixing and pulverizing 10.0 parts by weight of dodecamethylenediamine, 3.0 parts by weight of sodium dodecylbenzenesulfonate, 3.0 parts by weight of sodium ligninsulfonate, 14.0 parts by weight of white carbon and 70.0 parts by weight of bentonite, adding thereto a small amount of water, kneading the mixture, granulating by a granulator, and then drying.

Effects obtained by applying the polyamine compound of the present invention are shown below by test examples.

TEST EXAMPLE 10

(Reduction of cold—weather damage and frost damage)

| Effective ingredient in a crop-protecting composition | variously changed |
|---|---|
| Tested crops | Wheat & radish |
| Treating manner | Treatment of stems and leaves |

Air-dried and pulverized soil (passing a 2.5 mm$\phi$ sieve) was placed in holed pots of about 110 cm$^2$. Seeds of radish (Kind: Minowase-daikon) and wheat (Kind: Norin No. 61) were sown in respective pots, covered with the soil, and grown in a greenhouse (temperature: 17°–30° C.) up to the 4 true leaf-stage and the second true leaf emergence stage, respectively. Radish and wheat were adjusted to 5 and 15 in number, respectively.

On the other hand, crop-protecting composition (wettable powder type) prepared in the same manner as in Example 5 and containing polyamines shown in Tables 1 and 2 as effective ingredients were diluted with water to prepare crop-protecting composition liquids containing effective ingredients in the concentration shown in Tables 1 and 2.

Each of the thus prepared crop-protecting composition liquids was sprayed over the test plants to such degree that stems and leaves of test plants were almost uniformly wet (about 2.5 ml per pot).

After this treatment, the pots were transferred to the place of out-door conditions (−3°–7° C.) without the influence of rainfall.

With respect to radish, fresh weight above ground level was weighed 15 days after the stem-and-leaf treatment, and fresh weight ratio was determined taking the fresh weight in untreated area at the time of the stem-and-leaf treatment as 100. With wheat, fresh weight above ground level was weighed 14 days after the stem-and-leaf treatment, and fresh weight ratio was determined taking the fresh weight in untreated area as 100.

The results are shown in Tables 1 and 2.

From Tables 1 and 2, it is seen that the crop-protecting compositions of the present invention show remarkable effect of reducing cold-weather damage and frost damage.

TEST EXAMPLE 11

(Retardation of fading of green crops)

| Effective ingredient in a crop-protecting composition | variously changed |
|---|---|

|   -continued          |              |
|-----------------------|--------------|
| Tested crop           | Radish       |
| Treating manner       | Impregnation |

Crop-protecting compositions (aqueous formulation type) containing polyamines shown in Table 3 as effective ingredients were prepared in the same manner as in Example 3, and diluted to the concentrations shown in Table 3. The thus prepared liquids were poured into Petri dishes.

Matured leaves of radish (Kind: Hatsuka-Daikon) were cut into discs of 1 cm in diameter, and the resulting pieces were floated in the above-described Petri dishes with 8 pieces per 1 Petri dish, and then maintained under dark condition in an incubator of 25°±2° C. in temperature.

5 Days after floating the pieces, chlorophyll content in the pieces in each Petri dish was measured, and chlorophyll content ratio was determined taking the chlorophyll content at the start as 100.

The results are shown in Table 3.

TEST EXAMPLE 12

(Increase in green density)

| Effective ingredient in a crop-protecting composition | variously changed |
|---|---|
| Tested crop | Radish |
| Treating manner | Treatment of stems and leaves |

Air-dried and pulverized soil (passing a 2.5 mm$\phi$ sieve) was placed in holed pots of 15 cm in diameter. Seeds of radish were sown in pots, covered with soil, grown in greenhouse (temperature: 17°-30° C.) up to the third true leaf emergence stage, and then adjusted to 15 in number.

On the other hand, crop-protecting compositions (wettable powder type) containing polyamines shown in Table 4 as effective ingredients were prepared in the same manner as in Example 5, and subsequently diluted with water to prepare crop-protecting composition liquids containing the effective ingredients in the concentrations shown in Table 4. Each of the thus prepared liquids was sprayed over the radish to such degree that stems and leaves of the radish were almost uniformly wet (about 4 ml per pot).

11 Days after the treatment, fresh weight of radish above ground level and chlorophyll content were measured. Fresh weight ratio and chlorophyll content ratio were determined taking those in untreated area as 100.

The results are shown in Table 4.

Table 4 shows that many of the crop-protecting composition of the present invention can increase green density of radish.

TEST EXAMPLE 13

(Reduction of damage from photochemical oxidants)

| Effective ingredient in a crop-protecting composition | variously changed |
|---|---|
| Tested crop | Tobacco |
| Treating manner | Treatment of stems and leaves |

Air-dried and pulverized soil (passing a 2.5 mm$\phi$ sieve) was placed in holed pots of 15 cm in diameter. Seed of tobacoo (Kind: Bright-Yellow) were sown in the pots, covered with the soil, grown in a greenhouse (17°-30° C.) up to the 14-17 true leaf-stage, and then thinned to 5 in number.

On the other hand, crop-protecting compositions (wettable powder type) containing polyamines shown in Table 5 as effective ingredients were prepared in the same manner as in Example 5, and diluted with water to the concentrations shown in Table 5.

Each of the dilutions was sprayed over the test plants to such degree that stems and leaves of tobacco were sufficiently wet (about 4 ml per pot).

1 Day after the spraying, the plants were exposed to 0.3-0.4 ppm ozone for 2 hours under the conditions of 25,000 lux in illuminance and 20°-25° C. in temperature. Subsequently, they were cultivated for 3 days under outdoor conditions without the influence of rainfall; and damage with oxidant was examined with the naked eye. The rating was as follows. The case wherein no damages were observed was rated as 0, and the case wherein minute spots appeared all over the leaves as 5, with rating the intermediate cases as 1, 2, 3 and 4 in the order of the damage increasing.

Damage indexes of respective leaves were summed up, and damage index ratio was determined taking the sum of damage indexes in untreated area as 100. The results are shown in Table 5.

TEST EXAMPLE 14

(Reduction of wilting)

| Effective ingredient in a crop-protecting composition | variously changed |
|---|---|
| Tested crop | Mulberry |
| Treating manner | Spraying on leaves |

Sound leaves of mulberry cut from petioles and placed in a room not exposed direct to the sunlight, with the surface upward.

On the other hand, crop-protecting compositions (wettable powder type) containing polyamines shown in Table 6 as effective ingredients were prepared in the same manner as in Example 5, and then diluted with water to be concentrations shown in Table 6.

Separately, wettable powder was prepared in the same manner as in Example 5 except for omitting the polyamine ingredient, and then diluted with water to about the same concentration as described above (control area).

Each of the dilutions was sprayed over the mulberry leaves, with 5 leaves per 1 application.

1 Day after the treatment, wilting degree was rated according to the following standard. That is, the case wherein no wilting was observed was rated as 0, and the case wherein the leaves were completely wilted and withered to death as 5, with rating the intermediate cases as 1, 2, 3 and 4 in the order of wilting degree increasing.

Average damage indexes of 5 leaves with each application are shown in Table 6.

TABLE 1

(In case of radish)

| Effective ingredient | Concentration of effective ingredient (mol/l) | | | |
|---|---|---|---|---|
| | a | 2a | 4a | 8a |
| Tetramethylenediamine | 17.3 | 0.0 | 0.0 | 0.0 |
| Hexamethylenediamine | 26.2 | 0.0 | 0.0 | 0.0 |

TABLE 1-continued (In case of radish)

| Effective ingredient | Concentration of effective ingredient (mol/l) | | | |
|---|---|---|---|---|
| | a | 2a | 4a | 8a |
| Heptamethylenediamine | 64.8 | 36.7 | 22.3 | 0.0 |
| Octamethylenediamine | 97.1 | 93.0 | 81.2 | 0.0 |
| Nonamethylenediamine | 117.6 | 35.3 | 34.5 | 0.0 |
| Decamethylenediamine | 46.9 | 27.2 | 10.6 | 0.0 |
| Dodecamethylenediamine | 40.0 | 24.4 | 9.7 | 0.0 |
| Tetradecamethylenediamine | 18.4 | 10.0 | 0.0 | 0.0 |
| Octadecamethylenediamine | 20.3 | 10.1 | 0.0 | 0.0 |
| N,N'-diguanyl-1,8-diaminooctane | 41.0 | 11.0 | 0.0 | 0.0 |
| p,p-diaminomethylbiphenyl | 35.7 | 61.7 | 29.1 | 17.2 |
| Untreated | 16.8 | | | |

TABLE 2

(In case of wheat)

| Effective ingredient | Concentration of effective ingredient (mol/l) | | | |
|---|---|---|---|---|
| | a | 2a | 4a | 8a |
| Tetramethylenediamine | 121.4 | 93.6 | 90.7 | 84.9 |
| Hexamethylenediamine | 119.6 | 135.8 | 131.8 | 112.7 |
| Heptamethylenediamine | 124.5 | 124.3 | 87.5 | 89.7 |
| Octamethylenediamine | 121.1 | 148.7 | 172.4 | 149.6 |
| Nonamethylenediamine | 160.7 | 98.8 | 115.6 | 97.3 |
| Decamethylenediamine | 110.4 | 133.5 | 108.1 | 125.6 |
| Dodecamethylenediamine | 103.5 | 123.1 | 129.5 | 121.9 |
| Tetradecamethylenediamine | 117.9 | 131.0 | 125.4 | 124.8 |
| Octadecamethylenediamine | 122.0 | 121.3 | 110.0 | 103.1 |
| N,N'-diguanyl-1,8-diaminooctane | 135.1 | 126.2 | 110.3 | 100.0 |
| p,p'-diaminomethylbiphenyl | 131.3 | 141.6 | 124.6 | 113.8 |
| Untreated | 100 | | | |

Note: $a = 1.36 \times 10^{-2}$ in TABLES 1 and 2

TABLE 3

| Effective ingredient | Concentration of effective ingredient (mol/l) | | |
|---|---|---|---|
| | $\frac{1}{4} \times a$ | $\frac{1}{2} \times a$ | a |
| Tetramethylenediamine | 80.1 | 67.0 | 41.5 |
| Hexamethylenediamine | 71.2 | 70.4 | 51.3 |
| Octamethylenediamine | 85.1 | 97.9 | 77.0 |
| Decamethylenediamine | 50.0 | 81.3 | 70.4 |
| Dodecametnylenediamine | 41.9 | 72.0 | 70.0 |
| Unreated | | | 27.1 |
| At start | | | 100 |

Note: $a = 1.36 \times 10^{-2}$

TABLE 4

| Effective ingredient | Fresh weight ratio | | | Chlorophyll content ratio | | |
|---|---|---|---|---|---|---|
| | a | 2a | 4a | a | 2a | 4a |
| Tetramethylenediamine | 97 | 98 | 61 | 108 | 79 | 54 |
| Pentamethylenediamine | 133 | 132 | 69 | 166 | 152 | 63 |
| Hexamethylenediamine | 84 | 89 | 76 | 91 | 88 | 71 |
| Heptamethylenediamine | 116 | 104 | 91 | 101 | 91 | 91 |
| Octamethylenediamine | 117 | 119 | 100 | 123 | 131 | 96 |
| Nonamethylenediamine | 130 | 110 | 95 | 105 | 125 | 94 |
| Decamethylenediamine | 113 | 127 | 93 | 130 | 136 | 112 |
| Dodecamethylenediamine | 85 | 102 | 102 | 76 | 97 | 89 |
| Untreated | 100 | | | 100 | | |

Note: $a = 1.36 \times 10^{-2}$ (mol/l)

TABLE 5

| Effective ingredient | Concentration (g/l) | Damage index ratio |
|---|---|---|
| Tetramethylenediamine | 4 | 59 |
| | 2 | 36 |
| | 1 | 29 |
| Pentamethylenediamine | 4 | 63 |
| | 2 | 54 |
| | 1 | 31 |
| Hexamethylenediamine | 4 | 19 |
| | 2 | 35 |
| | 1 | 49 |
| Heptamethylenediamine | 4 | 30 |
| | 2 | 50 |
| | 1 | 78 |
| Octamethylenediamine | 4 | 9 |
| | 2 | 15 |
| | 1 | 23 |
| Decamethylenediamine | 4 | 8 |
| | 2 | 21 |
| | 1 | 25 |
| Dodecamethylenediamine | 4 | 20 |
| | 2 | 39 |
| | 1 | 41 |
| 1,8-diaminonaphthalene | 4 | 27 |
| | 2 | 29 |
| | 1 | 48 |
| 2,7-diaminofluorene | 4 | 38 |
| | 2 | 48 |
| | 1 | 91 |
| Untreated | | 100 |

TABLE 6

| Effective ingredient | Concentration (g/l) | Damage index |
|---|---|---|
| Tetramethylenediamine | 4 | 3 |
| | 1 | 2 |
| Hexamethylenediamine | 4 | 3 |
| | 1 | 3.5 |
| Octamethylenediamine | 4 | 0.5 |
| | 1 | 1.5 |
| Decamethylenediamine | 4 | 1 |
| | 1 | 2 |
| Dodecamethylenediamine | 4 | 2 |
| | 1 | 3 |
| Tetradecamethylenediamine | 4 | 2 |
| | 1 | 4 |
| Control | — | 5 |

What is claimed is:

1. A method for protecting a crop selected from the group consisting of a gramineous crop, radish, mulberry and tobacco from suffering damage selected from the group consisting of cold-weather damage, frost damage, fading of green color, damage from photochemical oxidants and wilting of leaves which comprises applying to a locus to be protected, in an amount sufficient to protect said crop, an alkylene diamine represented by the general formula:

$$H_2N-(CH_2)_n-NH_2$$

wherein n is an integer of 4-12.

2. The method of claim 1, wherein said alkylene diamine is applied in an amount of 0.1–1500 mols/hectare.

3. The method of claim 1, wherein said crop is wheat and said damage is cold-weather damage.

4. The method of claim 1, wherein said crop is wheat and said damage is frost damage.

5. The method of claim 1, wherein said crop is radish and said damage is cold-weather damage.

6. The method of claim 1, wherein said crop is radish and said damage is frost damage.

7. The method of claim 1, wherein said crop is tobacco and said damage is damage from photochemical oxidants.